(12) United States Patent
Voegele et al.

(10) Patent No.: US 7,441,973 B2
(45) Date of Patent: Oct. 28, 2008

(54) ADHESIVE APPLICATOR

(75) Inventors: James Walden Voegele, Cincinnati, OH (US); Mark S. Ortiz, Milford, OH (US); Fredrick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/551,261

(22) Filed: Oct. 20, 2006

(65) Prior Publication Data

US 2008/0095569 A1     Apr. 24, 2008

(51) Int. Cl.
    *B43K 5/14*     (2006.01)
(52) U.S. Cl. .................................... 401/134; 401/132
(58) Field of Classification Search .......... 401/132–135
    See application file for complete search history.

(56) References Cited

U.S. PATENT DOCUMENTS

| | | | |
|---|---|---|---|
| 3,792,699 A * | 2/1974 | Tobin et al. ................ 600/572 |
| 4,357,779 A * | 11/1982 | Maddock ...................... 47/1.5 |
| 4,735,616 A | 4/1988 | Eibl et al. |
| 4,766,898 A | 8/1988 | Hardy et al. |
| 4,874,368 A | 10/1989 | Miller et al. |
| 5,004,469 A | 4/1991 | Palmieri et al. |
| 5,154,320 A | 10/1992 | Bolduc |
| 5,254,113 A | 10/1993 | Wilk |
| 5,312,333 A | 5/1994 | Churinetz et al. |
| 5,324,305 A | 6/1994 | Kanner |
| 5,372,585 A | 12/1994 | Tiefenbrun et al. |
| 5,443,481 A | 8/1995 | Lee |
| 5,474,540 A | 12/1995 | Miller et al. |
| 5,529,577 A | 6/1996 | Hammerslag |
| 5,582,596 A | 12/1996 | Fukunaga et al. |
| 5,605,541 A | 2/1997 | Holm |
| 5,718,711 A | 2/1998 | Berenstein et al. |
| 5,752,965 A | 5/1998 | Francis et al. |

(Continued)

FOREIGN PATENT DOCUMENTS

EP     0315222 B1     11/1992

(Continued)

OTHER PUBLICATIONS

Ikeda, et al.; "Auxiliary Tool for Device for Applying Adhesive on Living Tissue;" published in Japan [translated abstract for Patent Application No. JP2000286958]; Jun. 12, 2001.

(Continued)

*Primary Examiner*—Huyen Le
(74) *Attorney, Agent, or Firm*—Frost Brown Todd LLC

(57) ABSTRACT

An apparatus for applying a liquid substance comprises a bulb portion, a cannulated shaft in fluid communication with the bulb portion, and a swab portion in fluid communication with the cannulated shaft. The bulb portion comprises a capsule. The capsule comprises a liquid substance. The bulb portion further comprises a valve operable to control the flow of a medium through the bulb portion. The bulb portion is operable to rupture the capsule to release the liquid substance. The cannulated shaft is dimensioned to extend percutaneously into a patient. The swab portion is operable to apply the liquid substance. The apparatus may be used to percutaneously apply adhesives to tissue, such as through a trocar or other cannulated member.

17 Claims, 9 Drawing Sheets

U.S. PATENT DOCUMENTS

| | | | |
|---|---|---|---|
| 5,759,169 A | 6/1998 | Marx | |
| 5,759,171 A | 6/1998 | Coelho et al. | |
| 5,814,022 A | 9/1998 | Antanavich et al. | |
| 5,844,087 A | 12/1998 | Zimmerman et al. | |
| 5,895,412 A | 4/1999 | Tucker | |
| 5,928,611 A | 7/1999 | Leung | |
| 5,981,621 A | 11/1999 | Clark et al. | |
| 6,007,515 A | 12/1999 | Epstein et al. | |
| 6,010,714 A | 1/2000 | Leung et al. | |
| 6,055,828 A | 5/2000 | Rivera et al. | |
| 6,099,807 A | 8/2000 | Leung | |
| 6,113,571 A | 9/2000 | Zinger et al. | |
| 6,143,352 A | 11/2000 | Clark et al. | |
| 6,143,805 A | 11/2000 | Hickey et al. | |
| 6,162,239 A | 12/2000 | Manhes | |
| 6,174,919 B1 | 1/2001 | Hickey | |
| 6,183,593 B1 | 2/2001 | Narang et al. | |
| 6,206,905 B1 | 3/2001 | Holm et al. | |
| 6,217,603 B1 | 4/2001 | Clark et al. | |
| 6,228,051 B1 | 5/2001 | Trumbull | |
| 6,234,994 B1 | 5/2001 | Zinger | |
| 6,245,933 B1 | 6/2001 | Malofsky et al. | |
| 6,280,399 B1 | 8/2001 | Rossin et al. | |
| 6,283,933 B1 | 9/2001 | D'Alessio et al. | |
| 6,302,898 B1 | 10/2001 | Edwards et al. | |
| 6,306,243 B1 | 10/2001 | Clark et al. | |
| 6,310,166 B1 | 10/2001 | Hickey et al. | |
| 6,322,852 B1 | 11/2001 | Leung | |
| 6,325,810 B1 | 12/2001 | Hamilton et al. | |
| 6,340,097 B1 | 1/2002 | D'Alessio et al. | |
| 6,352,704 B1 | 3/2002 | Nicholson et al. | |
| 6,372,313 B1 | 4/2002 | D'Alessio et al. | |
| 6,376,019 B1 | 4/2002 | Leung | |
| 6,394,975 B1 | 5/2002 | Epstein | |
| 6,394,982 B1 | 5/2002 | Ehrenfels | |
| 6,398,797 B2 | 6/2002 | Bombard et al. | |
| 6,412,639 B1 | 7/2002 | Hickey | |
| 6,420,590 B1 | 7/2002 | Badejo et al. | |
| 6,425,704 B2 | 7/2002 | Voiers et al. | |
| 6,428,233 B1 | 8/2002 | Clark et al. | |
| 6,428,234 B1 | 8/2002 | Bobo et al. | |
| 6,432,084 B1 | 8/2002 | Levinson et al. | |
| 6,433,096 B1 | 8/2002 | Hickey et al. | |
| 6,439,789 B1 | 8/2002 | Balance et al. | |
| 6,454,739 B1 | 9/2002 | Chang | |
| 6,455,064 B1 | 9/2002 | Narang et al. | |
| 6,458,095 B1 | 10/2002 | Wirt et al. | |
| 6,461,361 B1 | 10/2002 | Epstein | |
| 6,461,367 B1 | 10/2002 | Kirsch et al. | |
| 6,464,663 B1 | 10/2002 | Zinger | |
| 6,468,520 B1 | 10/2002 | Rowe et al. | |
| 6,471,670 B1 | 10/2002 | Enrenfels et al. | |
| 6,478,191 B1 | 11/2002 | D'Alessio et al. | |
| 6,488,197 B1 | 12/2002 | Whitman | |
| 6,488,650 B1 | 12/2002 | Epstein et al. | |
| 6,488,944 B2 | 12/2002 | Narang | |
| 6,491,201 B1 | 12/2002 | Whitman | |
| 6,494,896 B1 | 12/2002 | D'Alessio et al. | |
| 6,512,023 B1 | 1/2003 | Malofsky et al. | |
| 6,527,749 B1 | 3/2003 | Roby et al. | |
| 6,540,716 B1 | 4/2003 | Holm | |
| 6,547,467 B2 | 4/2003 | Quintero | |
| 6,565,840 B1 | 5/2003 | Clark et al. | |
| 6,579,469 B1 | 6/2003 | Nicholson et al. | |
| 6,585,967 B2 | 7/2003 | Narang et al. | |
| 6,589,269 B2 | 7/2003 | Zhu et al. | |
| 6,592,281 B2 | 7/2003 | Clark et al. | |
| 6,595,940 B1 | 7/2003 | D'Alessio et al. | |
| 6,602,496 B2 | 8/2003 | Hedgpeth et al. | |
| 6,605,667 B1 | 8/2003 | Badejo et al. | |
| 6,607,631 B1 | 8/2003 | Badejo et al. | |
| 6,613,020 B1 | 9/2003 | Holm et al. | |
| 6,616,019 B2 | 9/2003 | D'Alessio et al. | |
| 6,620,846 B1 | 9/2003 | Jonn et al. | |
| 6,637,967 B2 | 10/2003 | Bobo et al. | |
| 6,666,873 B1 | 12/2003 | Cassell | |
| 6,676,322 B1 | 1/2004 | Leung | |
| 6,681,979 B2 | 1/2004 | Whitman | |
| 6,695,199 B2 | 2/2004 | Whitman | |
| 6,705,790 B2 | 3/2004 | Quintero et al. | |
| 6,743,858 B2 | 6/2004 | Hickey et al. | |
| 6,746,667 B2 | 6/2004 | Badejo et al. | |
| 6,748,950 B2 | 6/2004 | Clark et al. | |
| 6,764,467 B1 | 7/2004 | Roby et al. | |
| 6,767,552 B2 | 7/2004 | Narang | |
| 6,779,657 B2 | 8/2004 | Mainwaring et al. | |
| 6,783,514 B2 | 8/2004 | Tovey et al. | |
| 6,802,416 B1 | 10/2004 | D'Alessio et al. | |
| 6,802,822 B1 | 10/2004 | Dodge | |
| 6,811,341 B2 | 11/2004 | Crane | |
| D500,085 S | 12/2004 | Cotter et al. | |
| 6,837,027 B2 | 1/2005 | Hickey | |
| 6,863,660 B2 | 3/2005 | Marx | |
| 6,884,232 B1 | 4/2005 | Hagmann et al. | |
| 6,896,684 B2 | 5/2005 | Monassevitch et al. | |
| 6,896,838 B2 | 5/2005 | D'Alessio | |
| 6,921,381 B2 | 7/2005 | Spero et al. | |
| 6,942,875 B2 | 9/2005 | Hedgpeth | |
| 6,960,040 B2 | 11/2005 | D'Alessio et al. | |
| 7,037,344 B2 | 5/2006 | Kagan et al. | |
| 2002/0012678 A1 | 1/2002 | Narang | |
| 2002/0037310 A1 | 3/2002 | Jonn et al. | |
| 2002/0048480 A1 | 4/2002 | D'Alessio et al. | |
| 2002/0055573 A1 | 5/2002 | Malofsky et al. | |
| 2002/0065336 A1 | 5/2002 | Hickey et al. | |
| 2002/0119184 A1 | 8/2002 | Nicholson et al. | |
| 2002/0147462 A1 | 10/2002 | Mair et al. | |
| 2002/0156203 A1 | 10/2002 | Hickey et al. | |
| 2002/0157675 A1 | 10/2002 | Clark et al. | |
| 2002/0165483 A1 | 11/2002 | Miller et al. | |
| 2002/0173770 A1 | 11/2002 | Flory et al. | |
| 2002/0176732 A1 | 11/2002 | Quintero et al. | |
| 2002/0176733 A1 | 11/2002 | Clark et al. | |
| 2002/0185396 A1 | 12/2002 | Mainwaring et al. | |
| 2002/0192011 A1 | 12/2002 | Bobo et al. | |
| 2002/0192107 A1 | 12/2002 | Hickey | |
| 2003/0007826 A1 | 1/2003 | Badejo et al. | |
| 2003/0007946 A1 | 1/2003 | Narang et al. | |
| 2003/0007947 A1 | 1/2003 | Narang | |
| 2003/0007948 A1 | 1/2003 | Hedgpeth | |
| 2003/0007949 A1 | 1/2003 | Hedgpeth et al. | |
| 2003/0015557 A1 | 1/2003 | D'Alessio et al. | |
| 2003/0031499 A1 | 2/2003 | Heard et al. | |
| 2003/0032833 A1 | 2/2003 | Badejo et al. | |
| 2003/0039781 A1 | 2/2003 | D'Alessio et al. | |
| 2003/0044219 A1 | 3/2003 | Quintero | |
| 2003/0060380 A1 | 3/2003 | Ayarza et al. | |
| 2003/0063944 A1 | 4/2003 | Leung | |
| 2003/0080151 A1 | 5/2003 | D'Alessio et al. | |
| 2003/0082116 A1 | 5/2003 | Badejo et al. | |
| 2003/0096069 A1 | 5/2003 | D'Alessio | |
| 2003/0149128 A1 | 8/2003 | Malofsky et al. | |
| 2003/0181964 A1 | 9/2003 | Sharkey et al. | |
| 2003/0202956 A1 | 10/2003 | Clark et al. | |
| 2004/0026282 A1 | 2/2004 | D'Alessio et al. | |
| 2004/0059283 A1 | 3/2004 | Kirwan et al. | |
| 2004/0111115 A1 | 6/2004 | Maw | |
| 2004/0120849 A1 | 6/2004 | Stewart et al. | |
| 2004/0137067 A1 | 7/2004 | Narang et al. | |
| 2004/0143290 A1 | 7/2004 | Brightbill | |
| 2004/0151688 A1 | 8/2004 | Sherbondy et al. | |
| 2004/0190975 A1 | 9/2004 | Goodman et al. | |
| 2004/0223932 A1 | 11/2004 | Hedgpeth et al. | |
| 2004/0223946 A1 | 11/2004 | Kidd et al. | |

| | | | |
|---|---|---|---|
| 2004/0234578 A1 | 11/2004 | Chen et al. | |
| 2004/0254561 A1 | 12/2004 | Stenton | |
| 2005/0033328 A1 | 2/2005 | Laufer et al. | |
| 2005/0042266 A1 | 2/2005 | Narang | |
| 2005/0047846 A1 | 3/2005 | Narang et al. | |
| 2005/0070935 A1 | 3/2005 | Ortiz | |
| 2005/0145671 A1 | 7/2005 | Viola | |
| 2005/0147457 A1 | 7/2005 | Badejo et al. | |
| 2005/0175395 A1 | 8/2005 | Quintero et al. | |
| 2005/0182443 A1 | 8/2005 | Jonn et al. | |
| 2005/0184121 A1 | 8/2005 | Heinrich | |
| 2005/0220849 A1 | 10/2005 | Hickey | |
| 2005/0228446 A1 | 10/2005 | Mooradian et al. | |
| 2005/0230453 A1 | 10/2005 | Viola | |
| 2005/0256446 A1 | 11/2005 | Criscuolo et al. | |
| 2006/0009099 A1 | 1/2006 | Jonn et al. | |

FOREIGN PATENT DOCUMENTS

| | | |
|---|---|---|
| EP | 0716833 A2 | 6/1996 |
| EP | 0648510 B1 | 11/1998 |
| EP | 0669100 B1 | 11/1998 |
| EP | 1078600 A2 | 2/2001 |
| EP | 1159081 A1 | 12/2001 |
| EP | 1381321 A2 | 1/2004 |
| EP | 1113839 B1 | 11/2004 |
| EP | 1073484 B1 | 8/2005 |
| EP | 1411836 B1 | 10/2005 |
| JP | 10262986 | 10/1998 |
| JP | 2000217830 | 8/2000 |
| JP | 2001157716 | 6/2001 |
| JP | 2001190558 | 7/2001 |
| JP | 2002233581 | 8/2002 |
| JP | 2003126268 | 5/2003 |
| JP | 2005028009 | 2/2005 |
| JP | 2005169125 | 6/2005 |
| WO | WO 92/09651 | 6/1992 |
| WO | WO 95/31137 A1 | 11/1995 |
| WO | WO 98/41154 A1 | 9/1998 |
| WO | WO 99/17833 A1 | 4/1999 |
| WO | WO 99/30629 A1 | 6/1999 |
| WO | WO 01/12257 A1 | 2/2001 |
| WO | WO 01/24869 A1 | 4/2001 |
| WO | WO 01/62158 A2 | 8/2001 |
| WO | WO 01/62162 A1 | 8/2001 |
| WO | WO 01/62333 A1 | 8/2001 |
| WO | WO 02/067785 A2 | 9/2002 |
| WO | WO 03/088845 | 10/2003 |

OTHER PUBLICATIONS

Ikeda, et al.; "Device for Applying Organism Tissue Adhesive;" published in Japan [translated abstract for Patent Application No. JP2000320375]; Jul. 17, 2001.

Gomibuchi, Makoto; "Medical Adhesive Applicator;" published in Japan [translated abstract for Patent Application No. JP11023146]; Aug. 8, 2000.

Ikeda, et al.; "Organism-Tissue Adhesive Applicator;" published in Japan [translated abstract for Patent Application No. JP2001033756]; Aug. 20, 2002.

Ikeda, et al.; "Biological Tissue Adhesive Applicator;" published in Japan [translated abstract for Patent Application No. JP2001323890]; May 7, 2003.

Arikawa, Seiki; "Biological Tissue Adhesive Applicator;" published in Japan [translated abstract for Patent Application No. JP2003273091]; Feb. 3, 2005.

Keller, Wilhelm A.; "Applicator for Dispensing Appliance;" published in Japan [translated abstract for Patent Application No. JP2004358509]; Jun. 30, 2005.

Sasaki, Hiroshi; "Adhesive Agent Applicator for Surgical Operation;" published in Japan [translated abstract for Patent Application No. JP09076817]; Oct. 6, 1998.

* cited by examiner

ADHESIVE APPLICATOR

BACKGROUND

Biosurgical adhesives have been used in a variety of ways in various medical procedures. An exemplary adhesive is disclosed in U.S. Pub. No. 2004/0190975, the disclosure of which is incorporated by reference herein. Similarly, a variety of devices and techniques have been used to deliver adhesives at various sites. While several systems and methods have been made and used for delivering adhesives, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
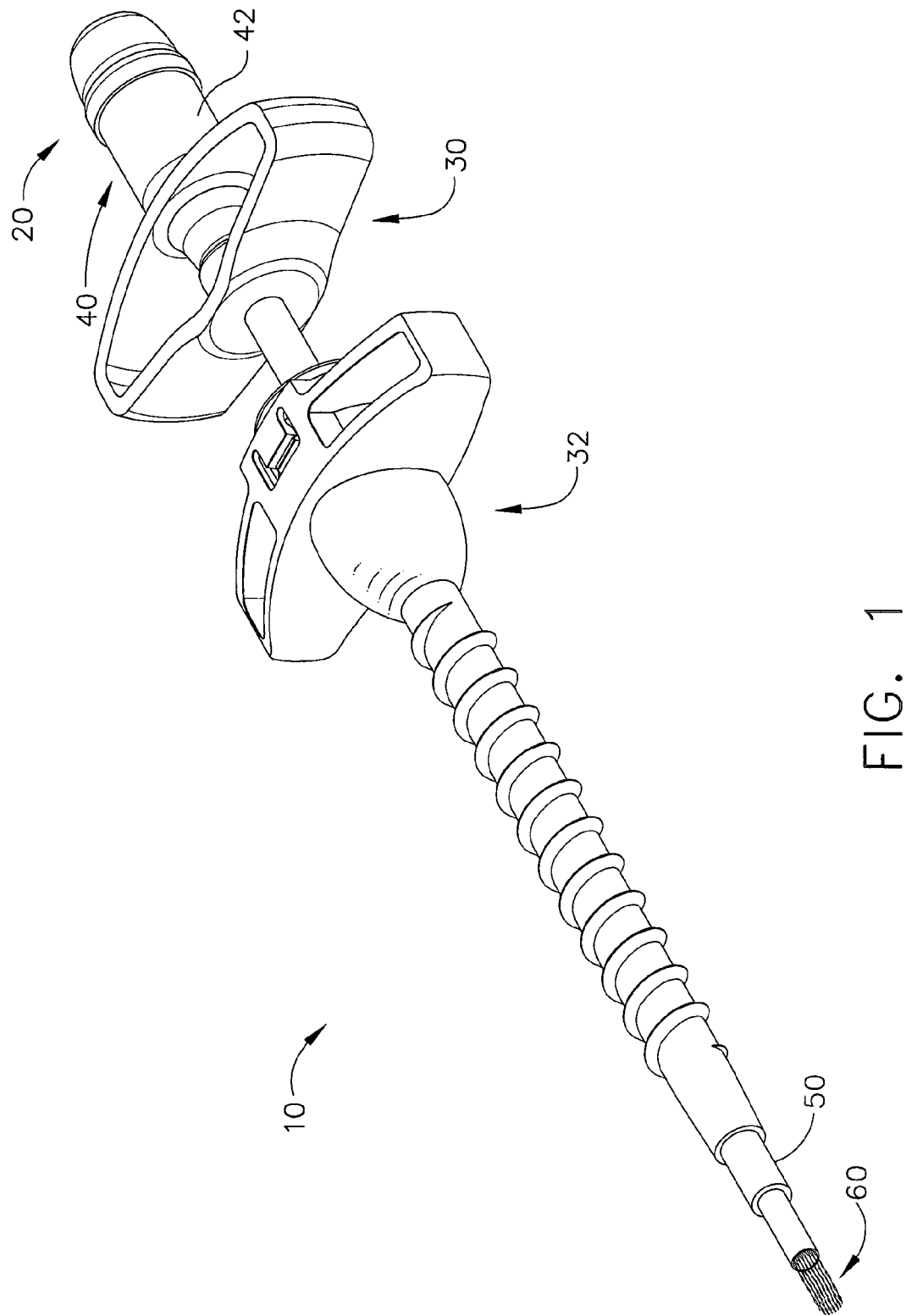
FIG. 1 depicts a perspective view of an exemplary adhesive delivery system.
Figure 2:
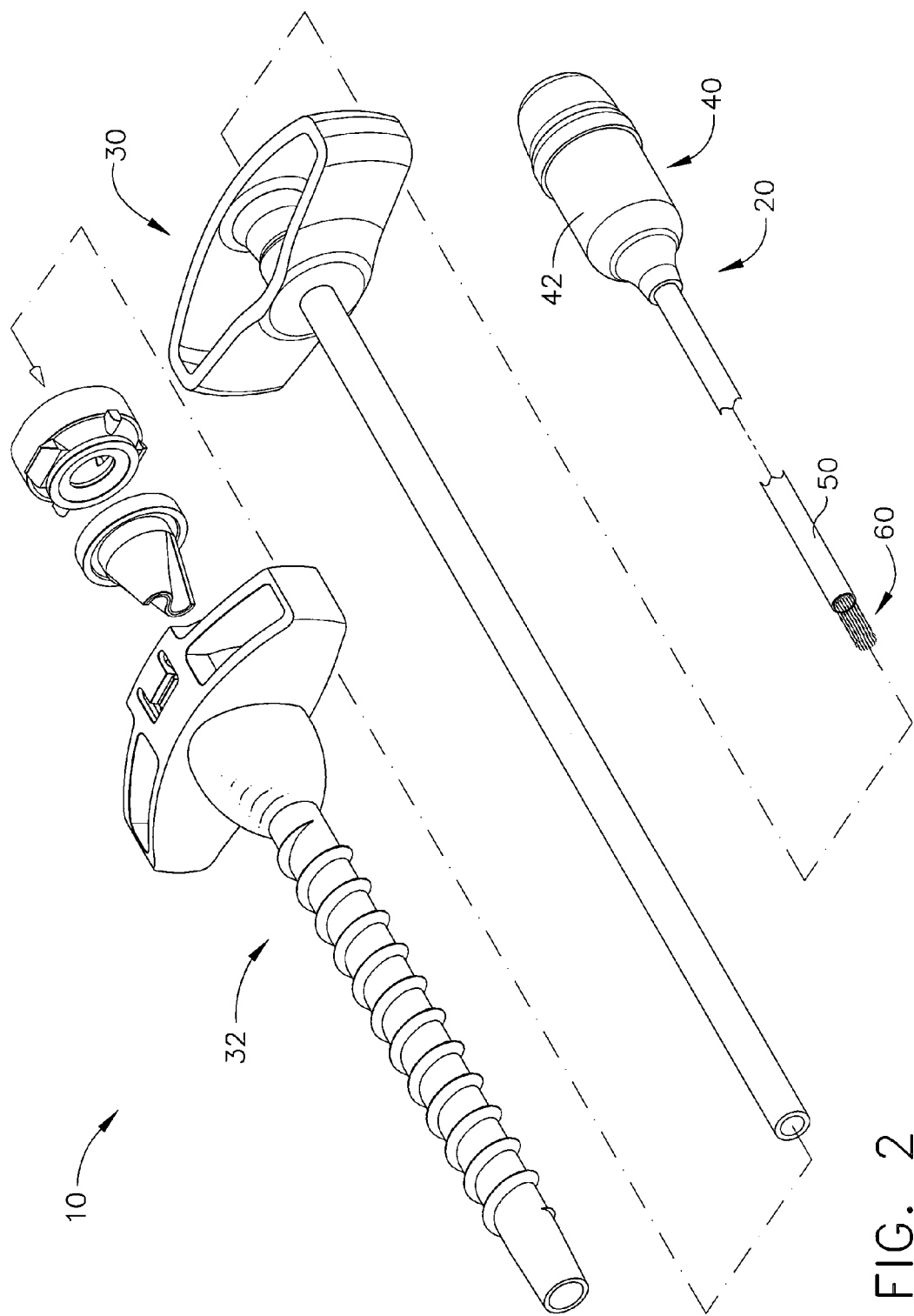
FIG. 2 depicts an exploded view of the adhesive delivery system of FIG. 1.
Figure 3:
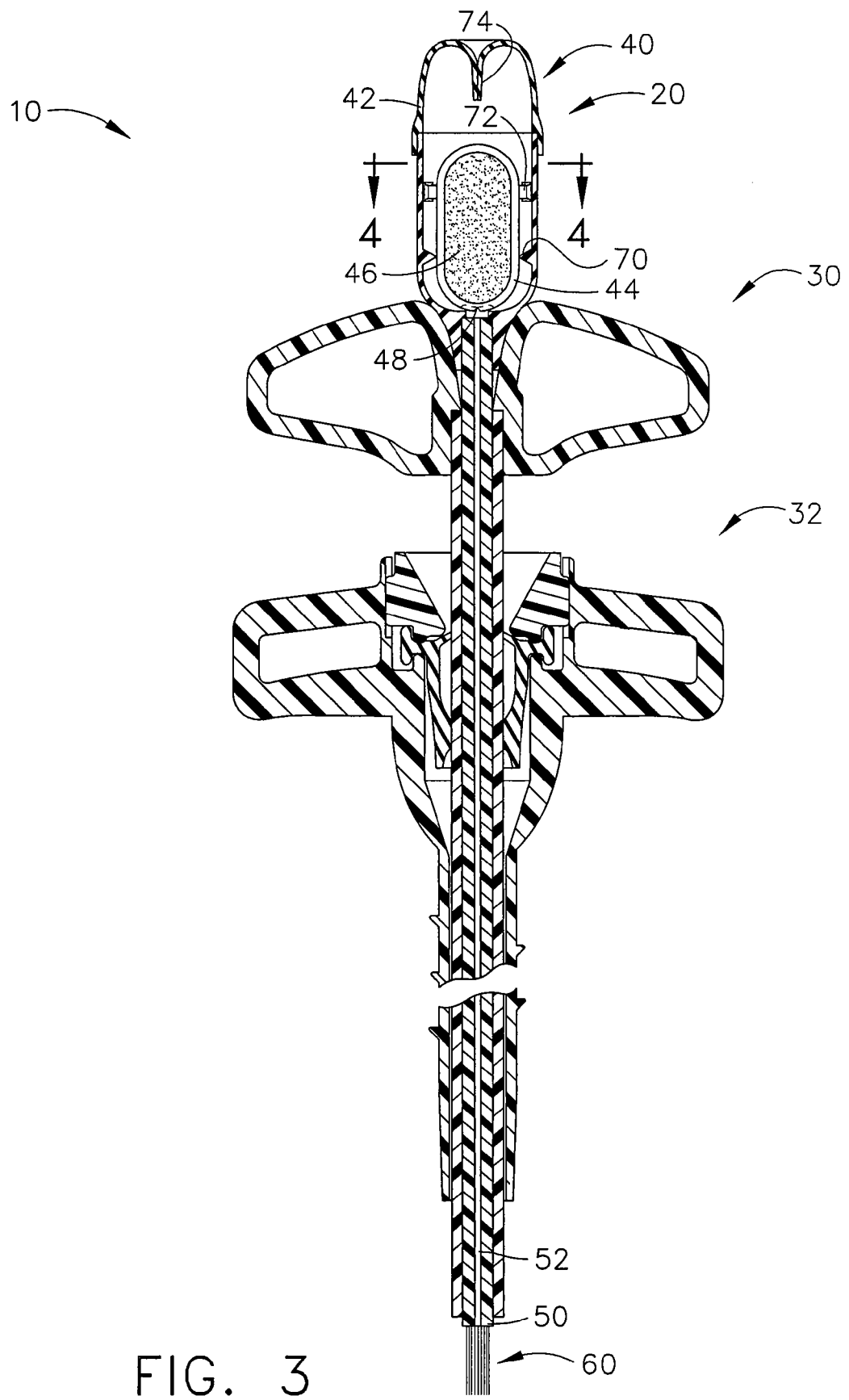
FIG. 3 depicts a cross-sectional view of the adhesive delivery system of FIG. 1.

As shown in FIGS. 1-3, an exemplary adhesive delivery system (10) comprises an applicator (20) inserted through a cannula member (30), which is inserted in a trocar (32). It will be appreciated that the particular cannula member (30) and trocar (32) that are depicted are shown for illustrative purposes only, and that applicator (20) of the present example may be used with any other type of cannula member (30) or trocar (32). Furthermore, cannula member (30) and trocar (32) are being shown merely to demonstrate that applicator (20) of the present example may be used in a minimally invasive surgical setting. It will also be appreciated that applicator (20) may be used without a cannula member (30) or trocar (32), such as in an open surgical setting.

Applicator (20) of the present example comprises a cannulated shaft (50), a bulb portion (40) at the proximal end of shaft (50), and a swab portion (60) at the distal end of shaft (50). Shaft (50) provides a conduit (52) for fluid communication from bulb portion (40) to swab portion (60). Shaft (50) is of sufficient length to permit applicator (20) be inserted through cannula member (30) and trocar (32), with swab portion (60) extending distally past the distal end of cannula member (30) and trocar (32), and with bulb portion extending proximally past the proximal end of cannula member (30) and trocar (32). However, any other suitable length for shaft (50) may be used.

Figure 4:
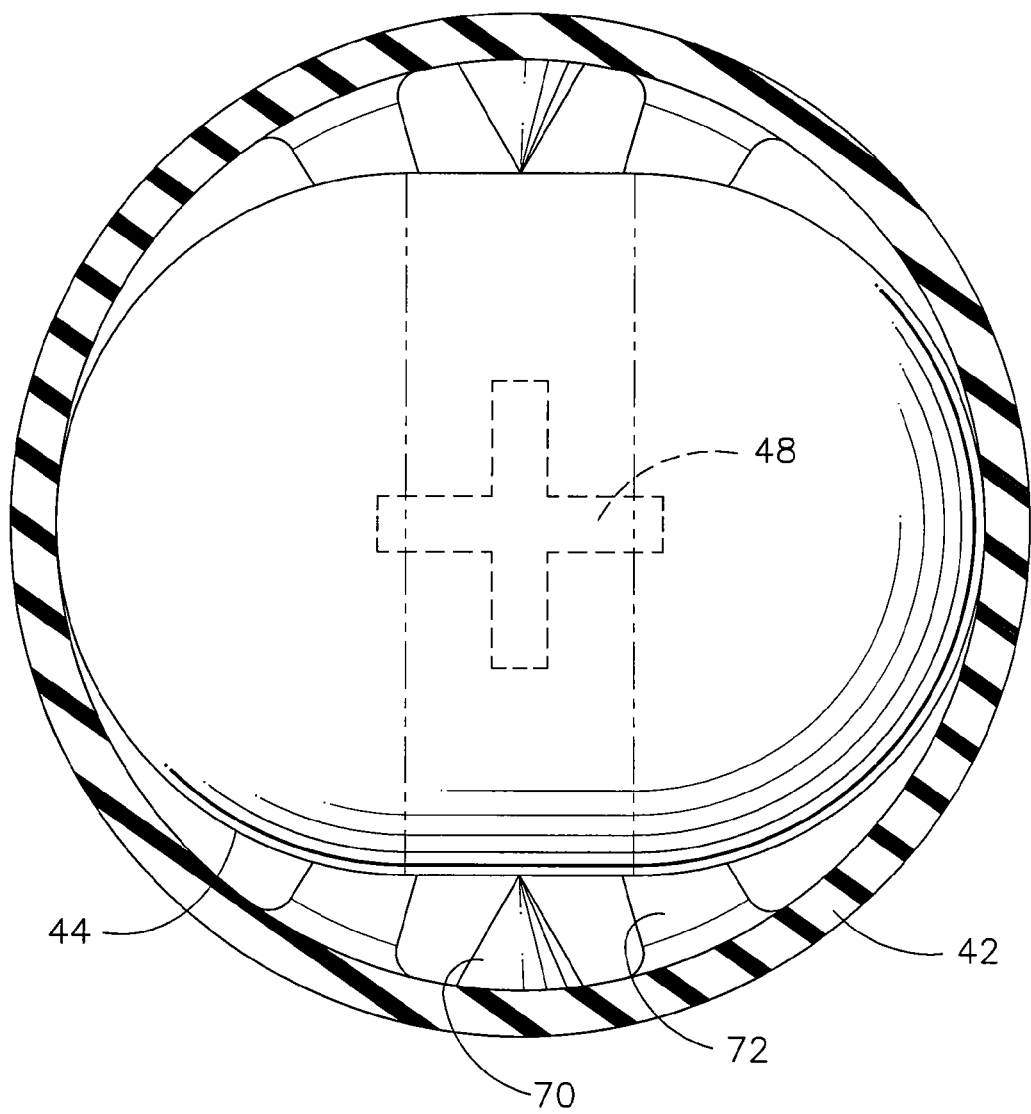
FIG. 4 depicts a cross-sectional view of the adhesive delivery system of FIG. 1, taken along line 4-4 of FIG. 3.

As shown in FIGS. 3-4, bulb portion (40) of the present example comprises a bulb (42) and a capsule (44). An adhesive (46) is provided within capsule (44). In the present example, adhesive (46) is configured to bond tissue. For instance, adhesive (46) may comprise a cyanoacrylate, an isocyanate, or any other suitable substance. Capsule (44) of the present example comprises a generally rigid but breakable material, such as glass or plastic. Alternatively, capsule (44) may be flexible, resilient, malleable, or have any other suitable properties. As will be described in greater detail below, capsule (44) of the present example is configured to break in order to communicate adhesive through conduit (52) of shaft (50). Capsule (44) further comprises a stress riser (48) configured to facilitate breaking of capsule (44). While stress riser (48) is shown as having a "plus sign" configuration, it will be appreciated that stress riser (48) may have any other suitable configuration. In addition, stress riser (48) may be substituted with any other feature, or may be omitted altogether.

Bulb (42) of the present example is formed of a generally resilient plastic material, though any other material (e.g., rubber, etc.) or combinations of materials having other suitable properties may be used. Bulb (42) has a pair of inwardly protruding spikes (70). Spikes (70) are configured to assist the breaking of capsule (44). It will therefore be appreciated that spikes (70) may be formed of a material having a greater hardness than that of remainder of bulb (42). Other piercing members or other suitable alternatives for spikes (70) will be apparent to those of ordinary skill in the art. Bulb (42) further comprises inwardly projecting retainers (72) configured to maintain the position of capsule (44) within bulb (42). A duckbill valve (74) is also provided in bulb (42) to permit air to be communicated into bulb (42) while preventing air from being communicated out of bulb (42). It will therefore be appreciated that bulb (42) may be used to break capsule (44) to release adhesive (46) upon initial squeezing of bulb (42) by a user; and to pump the released adhesive (46) through conduit (52) of shaft (50) upon repeated squeezing of bulb (42).

Figure 5:
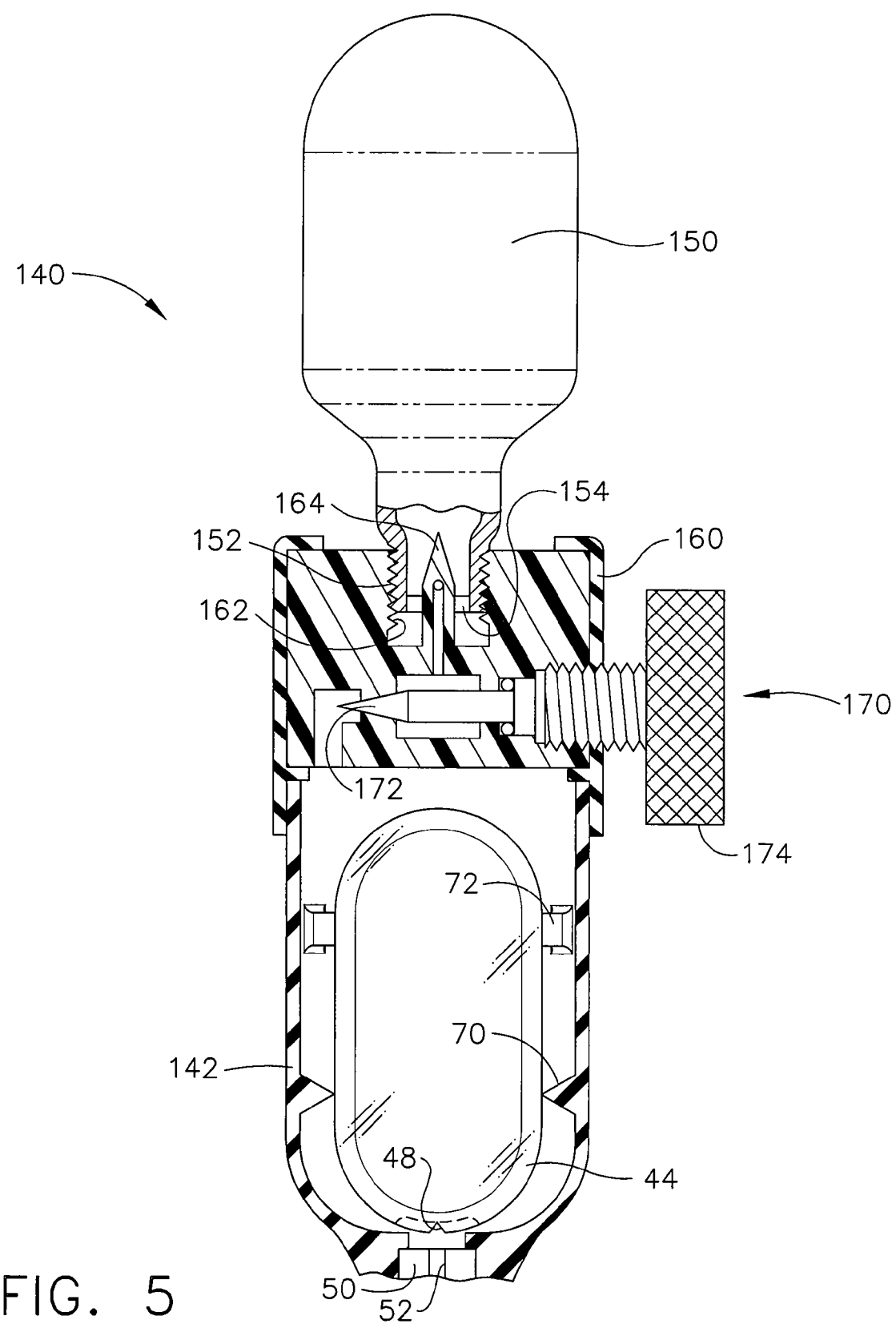
FIG. 5 depicts a cross-sectional view of the proximal end of an alternative adhesive delivery system.

A variation of bulb portion (40) is shown in FIG. 5. In this example, bulb portion (140) comprises a lower bulb portion (142) having spikes (70) and retainers (72) similar to bulb portion (40) described above. Bulb portion (140) also comprises capsule (44). However, instead of having a duckbill valve (74) for communicating adhesive through conduit (52) by repeated squeezing of bulb (42), a cartridge (150) is coupled with an upper member (160) of bulb portion (142). Cartridge (150) comprises a pressurized medium, such as a pressurized gas. Upper member (160) has threading (162) configured to engage with complimentary threading of cartridge (150), and an upwardly protruding cannulated spike (164) configured to pierce a seal (154) on cartridge (150). Cannulated spike (164) is in fluid communication with a needle valve assembly (170). Needle valve assembly (170) is also located in upper member (160), and comprises a needle (172) and a knob (174) for controlling axial positioning of needle (172). As will be apparent to those of ordinary skill in the art, needle valve assembly (170) may be used to controllably communicate pressurized medium from cartridge (150) to the interior of lower bulb portion (142). When adhesive (46) has been released from capsule (44), such controlled communication of pressurized medium from cartridge (150) may provide controlled communication of adhesive (46) through conduit (52) of shaft (50).

Figure 6:
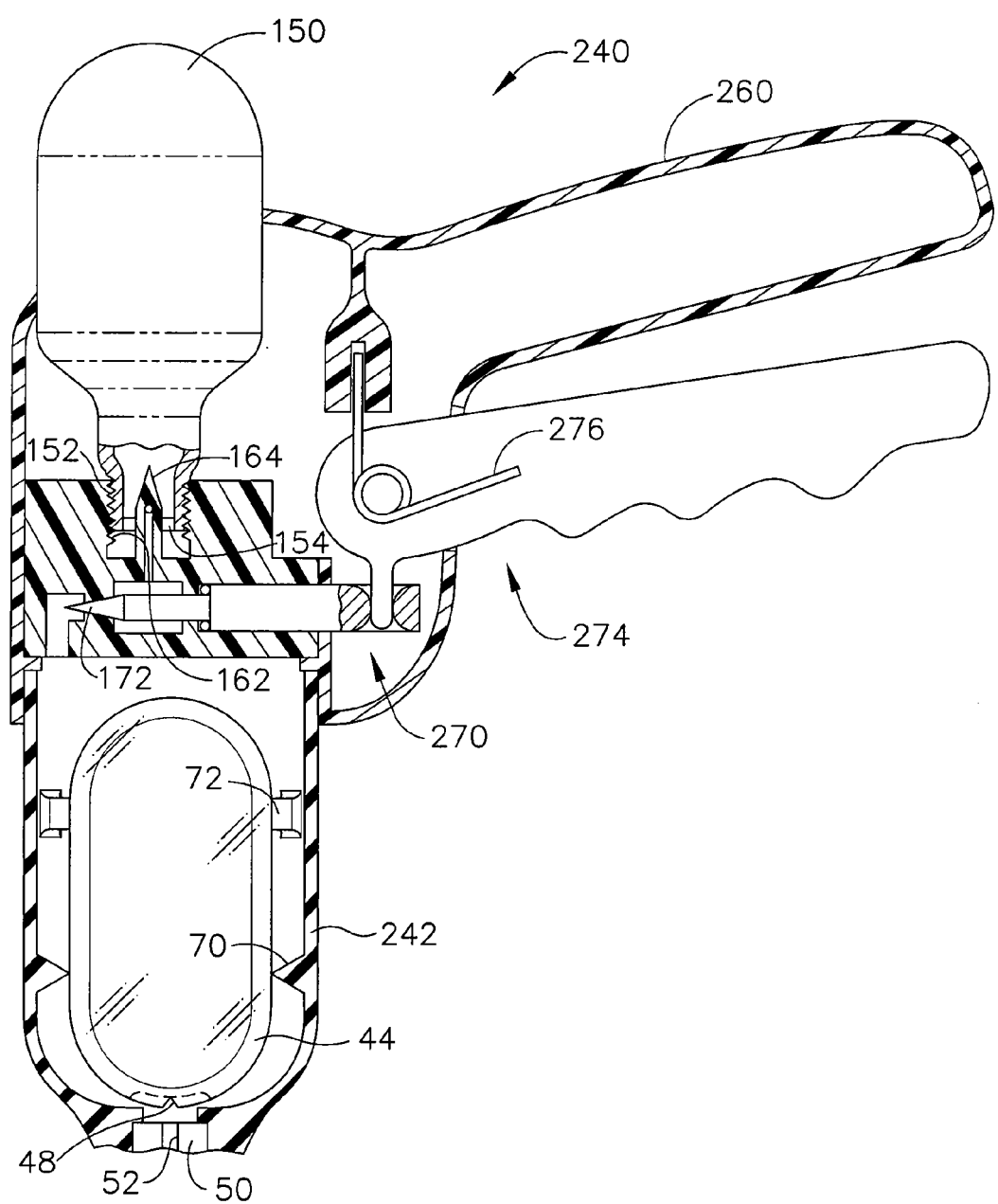
FIG. 6 depicts a cross-sectional view of the proximal end of an alternative adhesive delivery system.

Another variation of bulb portion (40) is shown in FIG. 6. In this example, bulb portion (240) comprises a lower bulb portion (242) having spikes (70) and retainers (72) similar to bulb portion (40) described above. Bulb portion (240) also comprises capsule (44), cartridge (150), and a needle valve assembly (270) for controllably communicating a pressurized medium from cartridge (150) to lower bulb portion (242). However, instead of having a knob (174) for controlling axial positioning of needle (172), bulb portion (240) has a pistol grip mechanism (274). Pistol grip mechanism (274) is part of a handle assembly (260) that is coupled with lower bulb portion (240). Pistol grip mechanism (274) comprises a spring (276) to bias needle valve assembly (270) to a closed position. As will be appreciated by those of ordinary skill in the art, pressurized medium from cartridge (150) may be communicated to lower bulb portion (240) as a function of the degree to which pistol grip mechanism (274) is actuated. When adhesive (46) has been released from capsule (44), such controlled communication of pressurized medium from cartridge (150) may provide controlled communication of adhesive (46) through conduit (52) of shaft (50).

Figure 7:
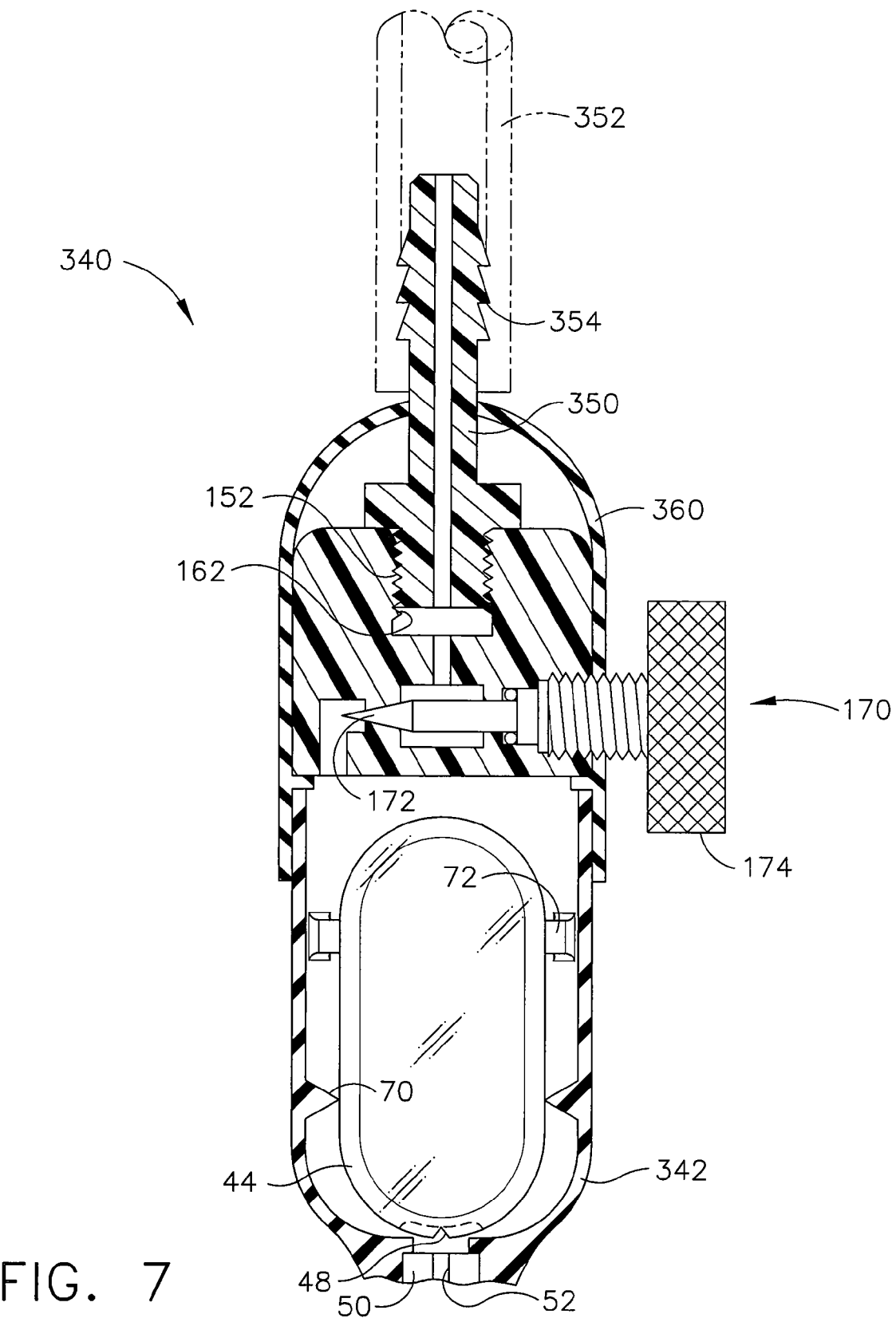
FIG. 7 depicts a cross-sectional view of the proximal end of an alternative adhesive delivery system.

Another variation of bulb portion (40) is shown in FIG. 7. In this example, bulb portion (340) comprises a lower bulb portion (342) having spikes (70) and retainers (72) similar to bulb portion (40) described above. Bulb portion (340) further comprises an upper bulb portion (360) having a needle assembly (170) similar to needle assembly (170) described above with respect to the embodiment shown in FIG. 5. However, instead of having a cartridge (150) disposed in upper bulb portion (360), upper bulb portion (360) comprises a barbed connector (350) in fluid communication with needle valve assembly (170). Barbed connector (350) is connectable with a tube (352), and has a plurality of barbs (354) configured to retain tube (352). Tube (352) may be in fluid communication with an external source (not shown) of a pressurized medium. As will be apparent to those of ordinary skill in the art, needle valve assembly (170) may be used to controllably communicate pressurized medium from tube (352) and barbed connector (350) to the interior of lower bulb portion (342). When adhesive (46) has been released from capsule (44), such controlled communication of pressurized medium from tube (352) and barbed connector (350) may provide controlled communication of adhesive (46) through conduit (52) of shaft (50).

While several structures and methods for communicating adhesive (46) to and through conduit (52) have been described above, it is contemplated that all of the foregoing structures and methods can be modified, substituted, or supplemented in a variety of ways. For instance, adhesive (46) may be communicated through conduit (52) via actuation of levers, finger triggers, thumb pushers, sliders, motorized actuators, etc. Other suitable alternatives will be apparent to those of ordinary skill in the art.

Figure 8:
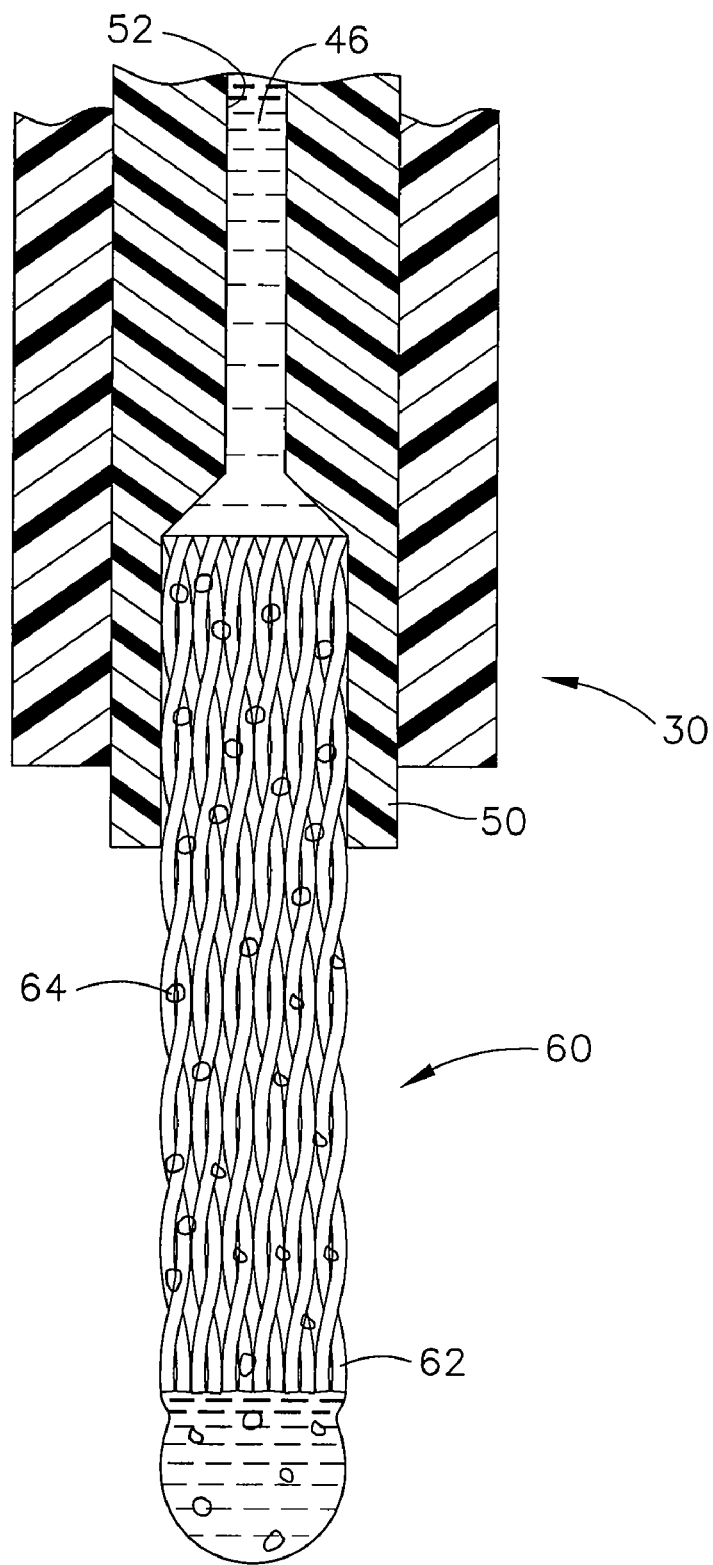
FIG. 8 depicts a cross-sectional view of the distal end of the adhesive delivery system of FIG. 1.

FIG. 8 shows an exemplary swab portion (60). Swab portion comprises a plurality of fibers (62) and an initiator or activator substance (64). Fibers (62) may be secured relative to shaft (50) in any suitable fashion. In another embodiment, swab portion (60) comprises a sponge-like or foam-like structure. In the present example, adhesive (46) and activator substance (64) are configured such that adhesive (46) will not satisfactorily adhere to structures (e.g., to tissue) absent exposure to activator substance (64). It will be appreciated, however, that alternative adhesives may be used, including those whose performance does not require any activator substance (64). It will also be appreciated that an activator substance (64) may be provided in a location other than swab portion (60). By way of example only, activator substance (64) may be provided within a bulb portion (40) or elsewhere. For instance, a separate conduit (not shown) may be provided in shaft (50) for communicating activator substance (64) to swab portion (60) in any suitable fashion. Other ways in which an activator substance (64) may be used and provided will be apparent to those of ordinary skill in the art.

Figure 9:
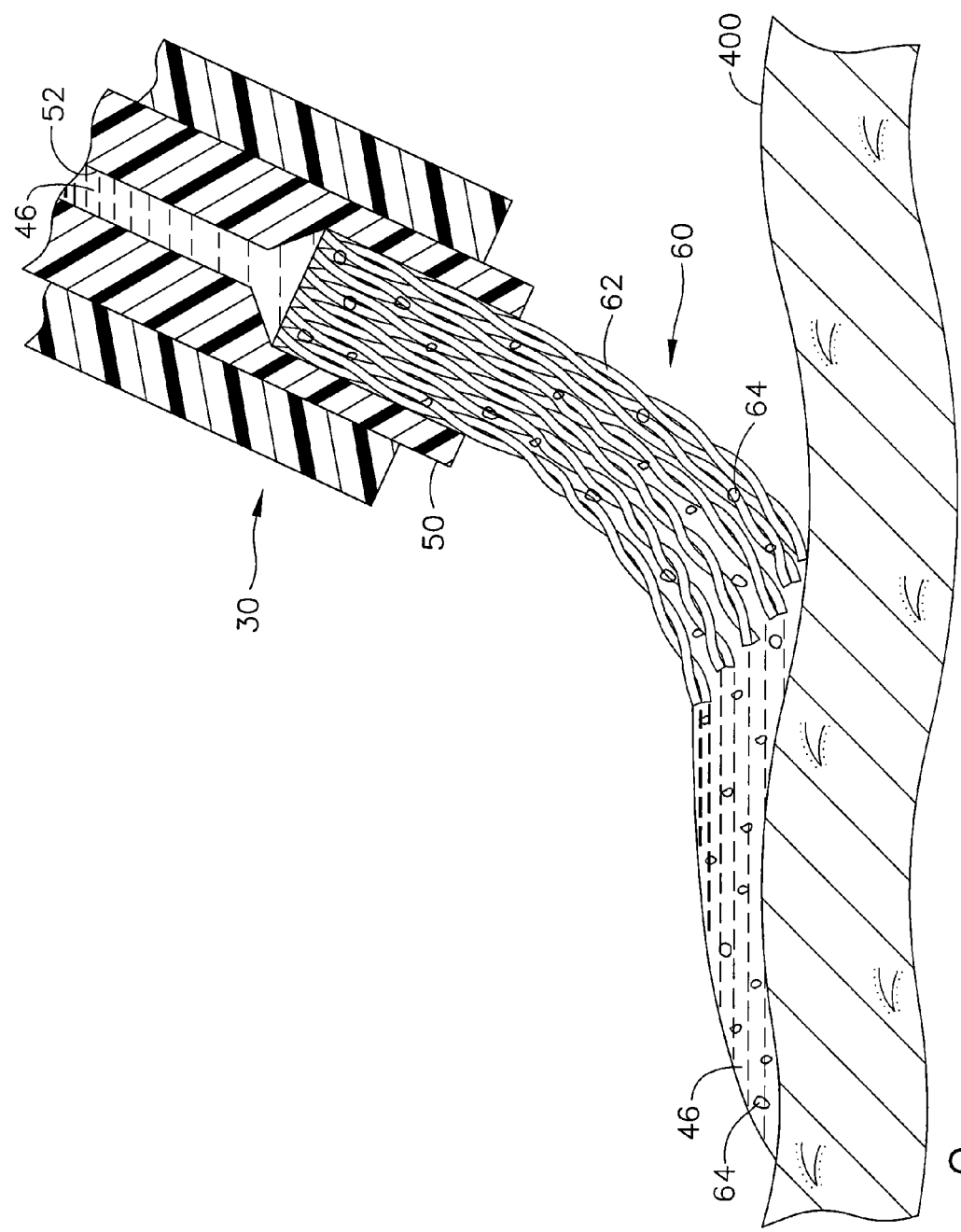
FIG. 9 depicts a cross-sectional view of the distal end of the adhesive delivery system of FIG. 1 in an exemplary use.

FIG. 9 depicts swab portion (60) in an exemplary use. As shown, swab portion (60) is being used to apply adhesive (46) to tissue (400). In the present example, an applicator (20) is used percutaneously and/or transmurally. Accordingly, it will be appreciated that any of the applicators (20) disclosed herein, including variations of the same, may be used in laparoscopic, endoscopic, open, or other surgical settings. Suitable uses for adhesive (46) or other substances applied through applicator (20) include, but are not limited to, the following: to provide superficial or other cover for tissue (e.g., as a "liquid bandage"), to attain cellular attachment, to become an implant, to serve as a volume or bulking filler, to increase in volume when dispensed with fluid having tamponade properties, to adjoin tissue with other tissue, to adjoin a man-made component with tissue, or to adjoin two man-made components. To the extent that adhesive (46) is used as a bandage, dispensation of such adhesive (46) may be a preliminary step to subsequent curing or alteration of the bandage by exposure to light, external frequencies, pressure waves, heat, other chemicals, etc.

It will also be appreciated that applicator (20) may be used to apply a variety of substances in addition to or as an alternative to an adhesive (46). For instance, applicator (20) may be used to apply a solid substance carried by a fluid carrier. Applicator (20) may also be used to apply mixed media. To the extent that applicator (20) is used to apply mixed media, such media may be mixed within applicator (20) using any suitable mixing structures and techniques, including manual, mechanical, automatic, or combinations thereof. Other suitable substances that applicator (20) may be used to apply include, but are not limited to, sealants, drugs, sclerosing agents, necrosing agents, coagulants, ablation agents, image enhancing agents such as ultrasound, CT, MRI, PET, X-Ray (radiographic), or radio pharmaceuticals. Other substances will be apparent to those of ordinary skill in the art. Furthermore, substances applied through applier (20) may be colored to make such substances easily observable by the naked eye or otherwise.

Any of the applicators (20) described herein, including variations of the same, may be used as a single dosage device, as a reloadable (e.g., single patient) device, or as a device that is otherwise reusable at least in part. Furthermore, while applicator (20) is described and shown as being axially dispensing, it will be appreciated that applicator (20) may be oriented fixedly or adjustable to a variety of positions or orientations.

To the extent that an applicator (20) needs to be withdrawn relative to trocar (32) (e.g., to insert another applicator (20) relative to trocar (32)), it may be desirable to prevent a used swab portion (60) from coming in contact with the trocar (32). To the extent that the distal end of cannula (30) extends distally beyond the distal end of trocar (32) in such situations, applicator (20) may be withdrawn relative to cannula (30), with cannula (30) remaining in a fixed axial position relative to trocar (32) at least until swab portion (60) has cleared the distal end of cannula (30). Cannula (30) may thus shield trocar (32) from swab portion (60). A new cannula (30) may thereafter be inserted with a new applicator (20). Other structures and methods for avoiding contact between swab portion (60) and trocar (32) will be apparent to those of ordinary skill in the art, to the extent that such contact is sought to be avoided.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. the sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. An apparatus for applying a liquid substance, the apparatus comprising:
   (a) a trocar;
   (b) a container portion, wherein the container portion comprises:
      (i) a capsule, wherein the capsule comprises a liquid substance, and
      (ii) a valve operable to control the flow of a medium through the bulb portion, wherein the container portion is operable to rupture the capsule to release the liquid substance from the capsule;
   (c) a cannula member disposed within the trocar;
   (d) a cannulated shaft disposed within the cannula member and in fluid communication with the container portion, wherein the cannulated shaft is dimensioned to extend percutaneously into a patient; and
   (c) a swab portion, wherein the swab portion is in fluid communication with the cannulated shaft, wherein the swab portion is operable to apply the liquid substance.

2. The apparatus of claim 1, wherein the capsule comprises a stress riser configured to facilitate the rupture of the capsule.

3. The apparatus of claim 1, wherein the container portion further comprises a piercing member operable to facilitate the rupture of the capsule.

4. The apparatus of claim 1, wherein the liquid substance comprises an adhesive.

5. The apparatus of claim 4, wherein the adhesive is a tissue adhering adhesive.

6. The apparatus of claim 1, wherein the valve comprises a duckbill valve.

7. The apparatus of claim 1, further comprising a pressurized medium source in communication with the valve.

8. The apparatus of claim 7, wherein the pressurized medium source comprises a cartridge.

9. The apparatus of claim 7, wherein the valve comprises a needle valve.

10. The apparatus of claim 7, further comprising a flexible tube, wherein the pressurized medium source is in fluid communication with the valve via the flexible tube.

11. The apparatus of claim 1, wherein the swab portion comprises a plurality of fibers.

12. The apparatus of claim 1, wherein the swab portion comprises an activator substance configured to react with the liquid substance.

13. A method of applying a liquid substance to tissue, the method comprising:
   (a) providing an applicator, wherein the applicator comprises:
      (i) a bulb portion, wherein the bulb portion comprises a capsule, wherein the capsule comprises a liquid substance, and a valve operable to control the flow of a medium through the bulb portion,
      (ii) a trocar;
      (iii) a cannula member disposed within the trocar;
      (ii) a cannulated shaft disposed within the cannula member and in fluid communication with the bulb portion, wherein the cannulated shaft is dimensioned to extend percutaneously into a patient, and a swab portion, wherein the swab portion is in fluid communication with the cannulated shaft, wherein the swab portion is operable to apply the liquid substance;
   (b) inserting a distal portion of the applicator percutaneously into a patient;
   (c) rupturing the capsule to release the liquid substance;
   (d) positioning the swab portion adjacent to tissue;
   (e) communicating the liquid substance through the cannulated shaft to the swab portion; and (f) applying the liquid substance to the adjacent tissue with the swab portion.

14. The method of claim 13, wherein the distal portion of the applicator is inserted through the trocar.

15. The method of claim 13, wherein the act of rupturing the capsule comprises squeezing the bulb portion.

16. The method of claim 13, wherein the act of communicating the liquid substance through the cannulated shaft comprises at least partially opening the valve.

17. The method of claim 13, wherein the liquid substance is an adhesive.

* * * * *